United States Patent [19]

Inoue et al.

[11] Patent Number: 4,752,417

[45] Date of Patent: Jun. 21, 1988

[54] METHOD FOR OPTICAL RESOLUTION OF PHENYLACETIC ACID DERIVATIVE

[75] Inventors: Ayumu Inoue, Aomori; Takeaki Umemura, Hyogo, both of Japan

[73] Assignee: Sumitomo Chemical Company, Limited, Osaka, Japan

[21] Appl. No.: 875,919

[22] Filed: Jun. 19, 1986

[30] Foreign Application Priority Data

Jun. 20, 1985 [JP] Japan ................................ 60-135718

[51] Int. Cl.$^4$ ............................................. C07B 57/00
[52] U.S. Cl. ................. 260/501.16; 560/105; 562/401; 562/402; 562/496
[58] Field of Search .............................. 562/401, 402; 260/501.16

[56] References Cited

U.S. PATENT DOCUMENTS 3,405,159 10/1968 Krieger et al. ................ 562/402 X
4,376,213 3/1983 Nohira et al. ........................ 562/401

FOREIGN PATENT DOCUMENTS 0107972 5/1984 European Pat. Off. .
55-136245 10/1980 Japan .
2013670 8/1979 United Kingdom .
2014137 8/1979 United Kingdom .

*Primary Examiner*—Werren B. Lone
*Assistant Examiner*—Vera C. Clarke
*Attorney, Agent, or Firm*—Sughrue, Mion, Zinn, Macpeak & Seas

[57] ABSTRACT

Alpha-isopropyl-p-chlorophenylacetic acid, which is an acid moiety of the pyrethroidal ester pesticides is subjected to optical resolution using optically active alpha-phenyl-beta-p-tolylethylamine or optically active alpha-phenylethylamine, as the optical resolution agent. The reaction of the acid with the amine is carried out in a hydrophobic organic solvent, such as aliphatic and aromatic hydrocarbons, in the presence of water, until the desired salt of the acid with the amine is separated therein through selective crystallization.

11 Claims, No Drawings

METHOD FOR OPTICAL RESOLUTION OF PHENYLACETIC ACID DERIVATIVE

This invention relates to a method for the resolution of alpha-isopropyl-p-chlorophenylacetic acid (ICPA). More particularly, it relates to a method for the optical resolution of ICPA using optically active alpha-phenyl-beta-p-tolylethylamine (PTE) or optically active alpha-phenylethylamine (PEA) in a hydrophobic organic solvent in the presence of water.

It has already been known that a group of alpha-substituted phenylacetic acid esters having a chemical structure greatly different from that of the conventional pyrethroidal insecticides has a strong insecticidal activity against various harmful insects (United Kindgom Pat. No. 1439615), and, among them, the esters of ICPA are particularly excellent in its efficacy and economy.

Furthermore, as to the insecticidal efficacy of the esters of the (+)- and (−)-carboxylic acids obtained by the optical resolution of its alpha-substituted phenylacetic acid moiety, it has been known that the ester of the (+)-acid exhibits about twice a strong insecticidal effect as compared with that of the ester of the (±)-acid, while the ester of (−)-acid is almost ineffective.

The present inventors have extensively studied to develop the optical resolution method which is expectedly more efficient from the commercial viewpoint, and have discovered that, in the method for optically resoluting ICPA using optically active PTE or optically active PEA, (+)-ICPA of a high optical purity could be obtained with satisfactory yield by using a hydrophobic solvent and operating in the presence of water. The present invention has been accomplished according to such findings.

Thus this invention provides a method for the optical resolution of ICPA, using optically active PTE or optically active PEA as the optical resolution agent, which method is characterized by that the reaction of the acid with the amine is carried out in a hydrophobic organic solvent in the presence of water, until one of the salts of the optically active ICPA with the amine is separated therein through selective crystallization.

According to the method of the present invention, one of the salt of the optically active ICPA with the amine can be obtained in high purity and in the form of readily filterable and (+)-ICPA of a high optical purity can be obtained without any additional purifying process such as recrystallization procedure.

As a secondary effect of the method of this invention, it is advantageous that the manufacturing and purifying processes of ICPA, if conducted in the method mentioned, for example, in the Japanese Unexamined Patent Publications Nos. 5350/1975 and 25535/1978, can be directly connected to the resolution process of this invention, wherein the ICPA solution in a hydrophobic organic solvent can be used as it is. Namely, as for the method for synthesizing ICPA, for example, as mentioned in the Japanese Unexamined Patent Publication No. 5350/1975, hydrolysis of alpha-isopropyl-p-chlorophenylacetonitrile has been known. And in the Publication No. 25535/1978, a method for purifying ICPA using benzene, toluene, xylene, chlorobenzene, hexane, heptane, or any other aliphatic or aromatic organic solvent has been disclosed. In conducting the method of this invention, it is not necessary to isolate the ICPA, and the solution of ICPA in an aliphatic or aromatic organic solvent used in the above refining method can directly be employed for the present optical resolution process.

Furthermore, since a hydrophobic organic solvent is used according to this method, it is extremely easy to recover the solvent. In this regard, this method is quite advantageous for conducting the optical resolution of ICPA in an industrial scale, in particular.

Thus, this invention relates to a method for the optical resolution of ICPA, which produces (+)-ICPA of a high optical purity at a high efficiency with constant yield, even when carried out in an industrial scale, together with various other commercial advantages.

The method of this invention will be further described below.

Examples of the hydrophobic organic solvents used in this invention include benzene, toluene, xylene and other aromatic hydrocarbons, and hexane, heptane, octane and other aliphatic hydrocarbons.

In this method, water is used in an amount ranging from 3 to 10 wt. %, based upon the amount of ICPA.

As the optically active PTE or PEA, (+)-PTE or (−)-PEA is preferable, and its amount is preferably in a range of 0.35 to 0.65 mol per mol of (+)- ICPA. The optical purity of these optical resolution agents may preferably be 92.0% e.e. or more.

Among these optical resolution agents, it is preferable to use (+)-PTE in an amount ranging from 0.45 to 0.65 mol per mol of (±)- ICPA, from the viewpoint of optical purity of (+)-ICPA to be obtained.

The reaction period of time is not particularly limited, if it is more than 30 minutes. The amount of the organic solvent is preferably in a range from 1 to 10 times by weight, more preferably, 2 to 4 times by weight, that of the ICPA used.

The method of this invention is conducted, for example, in the following procedure. In the first place, (±)-ICPA is caused to react with (+)-PTE or (−)-PEA in the solvent as mentioned above in the presence of appropriate amount of water. The temperature in this reaction is not limited, but it is desirable to keep the temperature at 40° to 150° C. during or after the reaction, in order to obtain (+)-ICPA of a higher optical purity. While keeping the temperature at 40° to 150° C., it is not necessary that the salt produced is completely dissolved. After keeping at the temperature, the precipitated salt of (+)-ICPA with the amine, preferably by cooling, is separated from the mother liquor. At this time, the ICPA remaining in the mother liquor is in the (−)-form. The separating temperature is preferably 0° to 60° C., or more preferably 10° to 30° C.

The salt of optically active ICPA may directly be used for the manufacturing process of an ester of ICPA, but, more preferably, the salt may be once transformed into an optically active ICPA or its alkaline salt by an ordinary method using an aqueous acid, such as aqueous hydrochloric acid and aqueous sulfuric acid, or an aqueous alkali, such as aqueous sodium hydroxide and aqueous potassium hydroxide, and then derived to an ester of ICPA.

This invention will be described below in further details by referring to the examples, to which, however, this invention is not limited. Meanwhile, the optical purity of ICPA shown in the following examples was determined by the method mentioned in Agric. Biol. Chem., 43, 2311 (1979), by Horiba et al., after decomposing the obtained salt of ICPA according to the ordinary method.

EXAMPLES 1-3

To 61.04 g of (±)-ICPA (chemical purity: 98.3%) was added 107.10 g of toluene, and the mixture was stirred to form a solution. Water was added thereto in an amount as described in Table 1. A solution of a described amount of (+)-PTE (optical purity: 95.0% e.e.) in 72.90 g of toluene was added to the above solution, and the mixed solution was heated up to 75° C. After keeping the temperature at 75° C. for one hour, the solution was allowed to cool at a rate of about 1° C./5 minutes. After reaching 20° C., the solution was held for one hour at the same temperature. The precipitated crystals were isolated by filtration, washed with a small volume of toluene, and dried. The salt of (+)-ICPA with (+)-PTE was obtained in an amount shown in Table 1.

At the same time, the similar operation was conducted without adding water, as a reference example.

TABLE 1

| Example No. | Amount of water used (g) | Amount of (+)-PTE used (g) | Obtained amount of (+)-ICPA-(+)-PTE salt | | Optical purity of ICPA obtained (% e.e.) |
| --- | --- | --- | --- | --- | --- |
| | | | Yield (g) | Yield (%) (vs. amount of (±)-ICPA) | |
| Example 1 | 2.4 | 31.24 | 37.68 | 31.5 | 94.6 |
| Example 2 | 6.0 | 31.24 | 37.29 | 31.2 | 94.4 |
| Example 3 | 2.4 | 37.37 | 47.53 | 39.7 | 93.6 |
| Reference example 1 | 0 | 31.24 | 39.78 | 33.3 | 89.8 |

To 35.00 g of the salt obtained in Example 1 in the above were added 60.00 g of toluene and 72.60 g of 5% aqueous sodium hydroxide solution, and the mixture was stirred at 40° C. for 1 hour. Then the reaction mixture was separated to an aqueous layer and a toluene layer. The aqueous layer was extracted with toluene and the toluene layer was combined with the toluene layer obtained in the above. The combined toluene layer was concentrated to give 17.39 g of (+)-PTE. The aqueous layer was acidified with 15% aqueous sulfuric acid and extracted with toluene. The toluene layer was washed with water and concentrated to give 17.53 g of (+)-ICPA.

EXAMPLE 4

To 61.04 g of (±)-ICPA (chemical purity: 98.3%) was added 107.10 g of toluene, and the mixture was stirred to make a solution. Then, 2.4 g of water was added thereto. A solution of 31.67 g of (+)-PTE (optical purity: 92.0% e.e.) in 72.90 g of toluene was added to the above solution, and the mixture was heated to 75° C. After keeping the temperature at 75° C. for one hour, the mixed solution was allowed to cool at a rate of about 1° C./5 minutes down to 20° C. Then the solution was held for additional one hour at 20° C. The precipitated crystals were isolated by filtration, washed with a small volume of toluene, and dried, to obtain the salt of (+)-ICPA with (+)-PTE in an amount shown in Table 2.

At the same time, the similar operation was conducted without adding water, as a reference example.

TABLE 2

| Example No. | Amount of water used (g) | Obtained amount of (+)-ICPA-(+)-PTE salt | | Optical purity of ICPA obtained (% e.e.) |
| --- | --- | --- | --- | --- |
| | | Yield (g) | Yield (%) (vs. amount of (±)-ICPA) | |
| Example 4 | 2.4 | 37.06 | 31.0 | 92.0 |
| Reference example 2 | 0 | 38.87 | 32.5 | 82.6 |

EXAMPLE 5

To 61.04 g of (-±)- ICPA (chemical purity: 98.3%) was added 107.10 g of toluene, and the mixture was stirred to make a solution. Then, 2.4 g of water was added thereto. A solution of 13.90 g of (−)-PEA (optical purity: 96.0% e.e.) in 72.90 g of toluene was added to the above solution, and the mixture was heated to 75° C. After keeping the temperature at 75° C. for one hour, the mixed solution was allowed to cool at a rate of about 1° C./5 minutes down to 20° C. Then the solution was held for additional one hour at 20° C. The precipitated crystals were isolated by filtration, washed with a small volume of toluene, and dried, to obtain the salt of (+)-ICPA with (−)-PEA in an amount shown in Table 3.

At the same time, the similar operation was conducted without adding water, as a reference example.

TABLE 3

| Example No. | Amount of water used (g) | Obtained amount of (+)-ICPA-(−)-PEA salt | | Optical purity of ICPA obtained (% of e.e.) |
| --- | --- | --- | --- | --- |
| | | Yield (g) | Yield (%) (vs. amount of (±)-ICPA) | |
| Example 5 | 2.4 | 33.44 | 35.5 | 87.0 |
| Reference example 3 | 0 | 32.68 | 34.7 | 81.8 |

We claim:

1. A method for the optical resolution of alpha-isopropyl-p-chlorophenylacetic acid, using optically active alpha-phenyl-beta-p-tolylethylamine or optically active alpha-phenylethylamine as the optical resolution agent, which method is characterized by that the reaction of the acid with the amine is carried out in a hydrophobic organic solvent in the presence of water, in the amount of 3-10 wt % based on the amount of alpha-isopropyl-p-chlorophenyloacetic acid until one of the salts of the optically active alpha-isopropyl-p-chlorophenylacetic acid with the amine is separated therein through selective crystallization.

2. A method for the optical resolution according to claim 1, wherein the said optically active alpha-phenyl-beta-p-tolylethylamine or optically active alpha-phenylethylamine is used in an amount of 0.35 to 0.65 mol per mol of alpha-isopropyl-p-chlorophenylacetic acid.

3. A method for the optical resolution according to claim 2, wherein (+)-alpha-phenyl-beta-p-tolylethylamine or (−)-alpha-phenylethylamine is used as the optical resolution agent.

4. A method for the optical resolution according to claim 3, wherein the hydrophobic organic solvent is one or more of solvents selected from the group consisting of aromatic hydrocarbons and aliphatic hydrocarbons.

5. A method for the optical resolution according to claim 3, wherein the hydrophobic organic solvent is an aromatic hydrocarbon.

6. A method for the optical resolution according to claim 5, wherein the solvent is used in an amount of 2 to 4 times by weight based upon the amount of alpha-isopropyl-p-chlorophenylacetic acid.

7. A method for the optical resolution according to claim 3, wherein (+)-alpha-phenyl-beta-p-tolylethylamine is used as the optical resolution agent.

8. A method for the optical resolution according to claim 7, wherein (+)-alpha-phenyl-beta-p-tolylethylamine is used in an amount of 0.45 to 0.65 mol per mol of alpha-isopropyl-p-chlorophenylacetic acid.

9. A method for the optical resolution according to claim 7, wherein the hydrophobic organic solvent is one or more of solvents selected from the group consising of aromatic hydrocarbons and aliphatic hydrocarbons.

10. A method for the optical resolution according to claim 7, wherein the hydrophobic organic solvent is an aromatic hydrocarbon.

11. A method for the optical resolution according to claim 10, wherein the solvent is used in an amount of 2 to 4 times by weight based upon the amount of alpha-isopropyl-p-chlorophenylacetic acid.

* * * * *